United States Patent
Braun et al.

[11] Patent Number: 5,079,379
[45] Date of Patent: Jan. 7, 1992

[54] FLUID BED PROCESS

[75] Inventors: John F. Braun, Houston; Robert T. Novak, Webster, both of Tex.

[73] Assignee: Monsanto Company, St. Louis, Mo.

[21] Appl. No.: 540,381

[22] Filed: Jun. 18, 1990

Related U.S. Application Data

[63] Continuation of Ser. No. 291,892, Dec. 29, 1988, abandoned.

[51] Int. Cl.$^5$ .................................................. C07C 253/26
[52] U.S. Cl. .................................... 558/324; 422/145
[58] Field of Search .............. 558/324, 320, 323, 325, 558/326

[56] References Cited

U.S. PATENT DOCUMENTS

| | | | |
|---|---|---|---|
| 3,164,626 | 1/1965 | Minekawa et al. | 260/465.3 |
| 3,335,169 | 8/1967 | Eden | 260/465.3 |
| 3,446,834 | 5/1969 | Caveterra et al. | 260/465.3 |
| 3,527,694 | 9/1970 | Luckenbach | 208/118 |
| 3,668,147 | 6/1972 | Voshino et al. | 252/432 |
| 4,018,712 | 4/1977 | Li | 252/456 |
| 4,102,914 | 7/1978 | Beuther et al. | 260/449.6 R |
| 4,225,531 | 9/1980 | Jones et al. | 260/449.6 R |
| 4,487,850 | 12/1984 | Li | 558/323 X |
| 4,545,943 | 10/1985 | Innes et al. | 558/323 X |
| 4,590,011 | 5/1986 | Li | 558/323 |
| 4,597,774 | 7/1986 | Garcia-Mallol et al. | 48/197 R |
| 4,725,409 | 2/1988 | Wolf | 422/145 |

FOREIGN PATENT DOCUMENTS 1474258 5/1977 United Kingdom .

OTHER PUBLICATIONS

Gldart et al., "The Effect of Fines on Entrainment from Gas Fluidised Beds", Dept. of Chemical Engineering, University of Bradford; Trans I Chem. E., vol. 57, (1979), pp. 269-275.

Primary Examiner—Joseph Paul Brust
Attorney, Agent, or Firm—Thomas N. Wallin

[57] ABSTRACT

Solids losses and particulate catalyst losses in fluidized bed catalytic reactors using cyclone means to retain catalyst are significantly reduced by the presence of particulate inert fines.

7 Claims, 1 Drawing Sheet

FLUID BED PROCESS

This is a continuation of application Ser. No. 97/291,892 filed Dec. 29, 1988, now abandoned.

BACKGROUND OF THE INVENTION

The present invention relates to improved fluid bed processes in which catalyst losses are significantly reduced. The invention is particularly advantageous in processes for ammoxidation of light hydrocarbons, preferably olefins, to unsaturated nitriles, such as acrylonitrile.

Many processes are known in which a bed of particulate catalyst is fluidized by a gaseous stream containing reactants which, in contact with the catalyst, are converted to desired reaction products. In such processes some catalyst, particularly smaller particle size catalyst, is entrained and must be separated from the product stream after it exits the fluid bed. This is frequently accomplished by cyclone means located downstream of the fluidized bed. Under the action of the cyclone, a major portion of the particulates are separated and recovered while the gaseous product stream passes overhead for further purification, utilization, or packaging. Unfortunately, during the process - most likely under severe conditions in the cyclone - a portion of the catalyst is converted to dust and exits the cyclone with the product stream and is thus considered lost. The problem is particularly apparent in ammoxidation processes where catalysts of relatively small particle sizes are frequently used. Such processes are exemplified, for example, in U.S. Pat. Nos. 3,164,626; 3,335,169; 3,446,834; 3,668,147; and 4,018,712; and 4,590,011; the teachings of which are incorporated herein by reference. U.S. Pat. No. 4,590,011 teaches the admixture of inert particulate materials with active catalyst, such as described above, to improve product yield and inhibit formation of by products.

It has long been apparent that techniques for reducing solids losses in fluid bed processes would represent a significant advance in the art.

SUMMARY OF THE INVENTION

The present invention resides in the discovery that catalyst losses in fluid bed reactors having cyclone means downstream of the fluidized bed are significantly reduced when the catalyst is mixed with a discrete, inert particulate material characterized by higher particle densities and lower particle sizes than the catalyst.

The invention will be understood from the following description of the preferred embodiments and the drawing in which FIG. 1 is a schematic representation of a fluid bed reactor having associated cyclone means.

DESCRIPTION OF THE PREFERRED EMBODIMENTS

Figure 1:
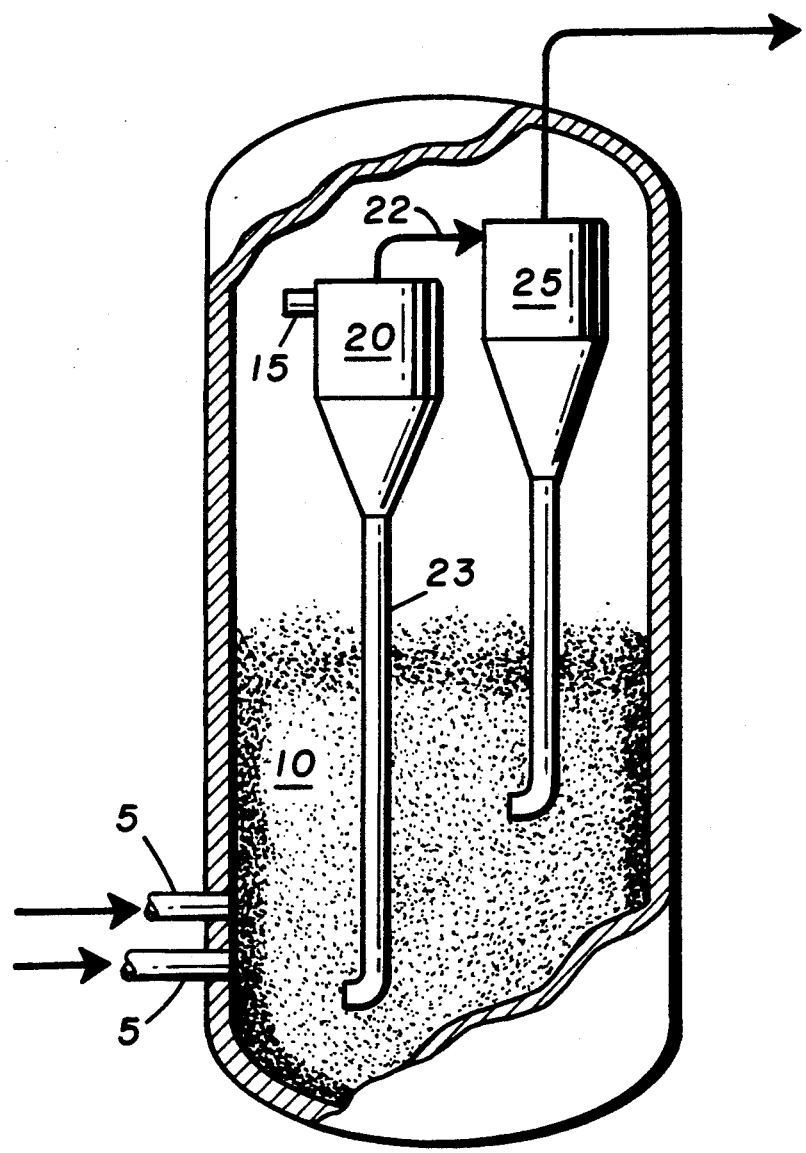

The present invention is an improvement in fluidized bed processes of the type in which a gaseous feed stream containing reactants is charged to a fluidized bed of particulate catalyst in a reactor system having cyclone means downstream of the fluidized exiting the fluidized bed.

The improvement is accomplished by use of a catalyst bed with discrete, inert, particulate material. The term "discrete" is used to designate an inert material separate from and not being a part of the catalyst particle. That is, catalyst support material and deactivated catalyst (unless present as separate particles) are not considered as constituting any portion of the discrete inert particulate material. The term "inert" is used to designate materials which do not catalytically or chemically substantially participate in or adversely affect the fluid bed reaction in which they are utilized.

The particle sizes, particle densities and quantity of inert particulates are selected such that loss of catalyst is at least 25% by weight lower than in an otherwise identical system not containing the inert material. This result can usually be obtained, for example, by selection such that the particulates exiting the bottom (dip leg) of the last cyclone means of the reactor system (a reactor system may have one or a plurality of cyclone means) comprise at least 5% of catalyst weight, preferably at least 5-65%, of inert materials. By way of further example, use of from 5% to 40% of catalyst weight of inert materials having a median particle size no larger and preferably smaller than the largest particle size of the particles constituting the 25% by weight of catalyst of lowest particle size distribution is generally found to give acceptable results. (The term "median particle size" is used in the conventional sense as explained at pages 14, 15 *Gas Fluoridation Technology*, D. Geldart—John Wiley, 1986 said disclosure being incorporated herein by reference.)

Inert particle densities higher than catalyst densities, preferably at least twice, and most preferably at least 2.3 times that of the catalyst are believed desirable to reduce catalyst losses.

Significant reductions in catalyst loss are generally achieved with 5% to 40% inert material. Higher quantities can be utilized but usually provide little additional reduction in catalyst loss. If desired, additional inert particles of sizes selected to promote optimum fluoridation and/or achieve improved yields and inhibit formation of byproducts as taught in U.S. Pat. No. 4,590,011 can be utilized.

The inert particles and catalyst can be mixed before being charged to the reactor or can be separately charged or added in any order.

A representative fluid bed reactor system is illustrated in FIG. 1 wherein gaseous reactants (diluted with inert diluents if desired) enter the system at opening 5; and pass through and fluidize a bed 10 of mixed catalyst and inert particles. Products, by products, unreacted reactants, and entrained particulates exit through conduit 15 into a first cyclone means 20 where a major portion of the particulates are separated and recovered at bottom exit 23. Exit gas and unseparated particulates flow through top exit 22 into a second cyclone 25 for further separation of gas and solids. The number of cyclones may be increased until further separation is not possible or is impractical. For purposes of this invention, the solids exiting the top of the last cyclone used in a system are considered "lost". Such solids are, in fact, considered lost in a practical sense in most commercial processes.

For purposes of specific description, the invention is hereinafter described with reference to its use in an ammoxidation process employing a catalyst disclosed in U.S. Pat. No. 4,018,712. It will be understood that the inventive concept is also applicable to other systems. The catalyst employed has the empirical formula

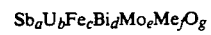

in which $M_e$ is nickel or cobalt, a is 1 to 10, b is 0.1 to 5, c is 0.1 to 5, d is 0.001 0.1, e is 0.001 to 0.1, f is 0 to 0.1, and g is a number taken to satisfy the valences of the quantities of the other components present.

The inert material that is added can be any particulate which does not unduly interfere with the fluidizing properties of the catalyst used in the fluid bed, and which imparts no undesirable catalytic activity and has no undesirable chemical reactivity. Especially preferred is the use of low surface area alpha-alumina. The preferred physical properties of the alpha-alumina are set forth hereafter.

One convenient method of preparing the catalyst is to first combine the oxides, sulfates, or the like of antimony, uranium, iron, and bismuth with sulfuric acid. When antimony sulfate is used as a starting material, it can be added to water wherein sulfuric acid is obtained. Nitric acid is used to oxidize the sulfate salts of the various elements or to further oxidize the oxides of the elements. Instead of using sulfuric acid to digest the metal oxides, nitric acid can be used. After the acid mixture has digested, the pH of the mixture is adjusted to the basic side to cause precipitation of the oxides. The precipitate is then filtered. After the filtering operation, the filter cake is dried at a suitable temperature of from about 100°–180° C. A catalyst support may be added prior to or subsequent to drying. A suitable drying temperature is about 110° C. However, drying can be obtained at higher temperatures such as up to about 650° C. The time over which drying is accomplished can range from an hour up to about 50 hours or more. Drying of the catalyst with or without the support can be advantageously accomplished, for example, by spray drying. The catalyst is calcined at a temperature in the range of about 500°–115° C. The time of calcination can vary and depends upon the temperature employed. Generally, a time period of 1–24 hours at a selected temperature is sufficient. The calcination is preferred to be conducted in the presence of oxygen or air. The catalyst is shaped to suitable particle size having a desired surface area.

The inert material may be mixed with the catalyst before addition to the reaction zone or inert material and catalyst can be added separately. Preferably the catalyst has a surface area of about 10–100 mz/g, a packed density of 0.9–1.1 g/ml, and an average particle size of 40–80 microns. The inert material has a surface area of less than 5mz/g, preferably of about 0.5–3m$^2$/g, a packed density of 0.5 to 2.5 g/l but preferably in the range of 0.9–2.5 g/ml, and a median particle size of less than 150 microns, preferably of about 15–55 microns.

The catalyst mixed with the inert material exhibits utility in the conversion of olefins with or without the presence of ammonia. The olefins employed as reactants for the conversion by the catalyst may be open chain, as well as cyclic and include, for example, propylene, butene-1, butene-2, isobutene, pentene-1 pentene-2, 3-methyl butene-1, 2-methyl butene-2, hexene-1, hexene-2, 4-methyl pentene-1, 3,3-dimethylbutene-1, 4-methyl pentene-2, octene-1, cyclopentene, cyclohexene and the like. Of course, mixtures of olefins and mixtures of olefins with other hydrocarbons may be employed. When the catalyst and inert mixture of the present invention is to be used for ammoxidation, the olefins mentioned above are applicable. However, the system exemplified is particularly adapted to the conversion of propylene with ammonia and oxygen to acrylonitrile at 250°–650° C.

The molar ratio of oxygen to the olefin in the feed will generally be in the range of 0.5:1 to 4:1 with a preferred ratio 1 being 1:1 to 3:1. The molar ratio of ammonia to olefin in the feed will generally be in the range of 0.5:1 to 5:1 and preferably slightly over the stoichiometric ratio of 1:1 ammonia:olefin will be employed.

While ammonia is most generally employed as the nitrogen providing compound, other nitrogen containing materials may be employed which chemically change to produce reactive nitrogen under the selected reaction conditions. Any source of oxygen, pure or in admixture with inert gases, may be employed in the process of the invention. Air is a suitable source of oxygen.

EXAMPLE 1

Inert fines (white, fused, blocky shaped, 99.5% by weight, alpha aluminum oxide particles) having a particle size distribution as shown in Table 1, below, are added to a fluid bed reactor containing ammoxidation catalyst having the empirical formula $Sb_1U_{0.18}Fe_{0.3-7}Bi_{0.01}Mo_{0.02}O$ sufficient on 50% by weight $SiO_2$ support. Adjustments are made to the catalyst and inert fines inventory in the reactor to obtain a desired propylene conversion and provide the amounts of each shown in Table 1 below. The catalyst has a packed density (determined by addition of a weighted quantity of catalyst to a graduated cylinder and tapping the cylinder until no further reduction in volume is observed) of 0.98 gm/ml and the inert fines a packed density of 2.2 gm/ml. Particle density of the catalyst is 1.6 gm/ml and that of the inert fines is 3.9 gm/ml.

A reaction mixture of propylene, air and ammonia is passed through the reactor at the velocity indicated in the Table.

The exit stream from the reactor is divided and passed through separate sets of three cyclones in series. Total solids losses from the system and losses of inert fines are measured and are shown in Table 1 in which all percentages are by weight unless otherwise indicated.

TABLE 1

| | Particle Size Distributions | |
| --- | --- | --- |
| Size | CATALYST Cumulative weight less than size indicated | INERT FINES Cumulative weight less than size indicated |
| 176.0 | 100.0 | 100.0 |
| 125.0 | 99.6 | 100.0 |
| 88.0 | 88.0 | 99.7 |
| 62.0 | 55.0 | 95.9 |
| 44.0 | 20.5 | 79.1 |
| 31.0 | 2.0 | 45.6 |
| 22.0 | 0.0 | 17.8 |
| 16.0 | 0.0 | 5.5 |
| 11.0 | 0.0 | 2.2 |
| 7.8 | 0.0 | 1.2 |

TABLE 1-continued

| Particle Size Distributions | | |
|---|---|---|
| 5.5 | 0.0 | 0.3 |
| 3.9 | 0.0 | 0.3 |
| 2.8 | 0.0 | 0.3 |
| median particle size | 59.4 microns | 32.8 microns |

EXAMPLE I

| | Run 1 | Run 2 | Run 3 | Run 4 | Run 5 | Run 6 |
|---|---|---|---|---|---|---|
| Catalyst charge, kg | 17450 | 16100 | 17500 | 16770 | 14000 | 12800 |
| Inert fines charge, kg | 0 | 0 | 0 | 1266 | 5756 | 6759 |
| Fluid Bed Inert Fines % | 0 | 0 | 0 | 7 | 29 | 35 |
| Final Cyclone Inert Fines % | 0 | 0 | 0 | nd* | nd | 63 |
| Velocity, m/sec | 0.57 | 0.59 | 0.62 | 0.59 | 0.59 | 0.60 |
| Reactor Temperature, C. | 464 | 464 | 461 | 464 | 463 | 464 |
| Reactor Pressure, atmosphere | 1.95 | 2.06 | 2.05 | 1.97 | 1.99 | 2.02 |
| Total Solids Loss, kg/day | 14.1 | 16.6 | 27.1 | 3.2 | 3.6 | 6.8 |
| % of loss that is inert fines | 0 | 0 | 0 | nd | nd | 47 |

*not determined

EXAMPLE 2

The test Example 1 is repeated using catalyst and fines having particle size distributions as shown in Table 2.

TABLE 2

| | Particle Size Distributions | |
|---|---|---|
| | CATALYST | INERT FINES |
| Size | Cumulative weight % less than size indicated | Cumulative weight % less than size indicated |
| 176.0 | 100.0 | 100.0 |
| 125.0 | 98.5 | 100.0 |
| 88.0 | 88.0 | 99.6 |
| 62.0 | 57.1 | 97.0 |
| 44.0 | 20.5 | 81.6 |
| 31.0 | 3.8 | 48.5 |
| 22.0 | 3.2 | 19.2 |
| 16.0 | 1.9 | 6.3 |
| 11.0 | 0.0 | 3.7 |
| 7.8 | 0.0 | 1.9 |
| 5.5 | 0.0 | 1.1 |
| 3.9 | 0.0 | 0.6 |
| 2.8 | 0.0 | 0.2 |
| median particle size | 58.5 microns | 31.6 microns |

EXAMPLE 2

| | Run 7 | Run 8 | Run 9 | Run 10 | Run 11 | Run 12 | Run 13 | Run 14 |
|---|---|---|---|---|---|---|---|---|
| Catalyst charge, kg | 19000 | 18500 | 18300 | 17700 | 17100 | 16900 | 17400 | 17200 |
| Inert fines, charge kg | 0 | 0 | 0 | 0 | 2164 | 1987 | 1814 | 1406 |
| Fluid Bed Inert Fines % | 0 | 0 | 0 | 0 | 11 | 10.5 | 9.5 | 7.6 |
| Final Cyclone Inert Fines, % | 0 | 0 | 0 | 0 | nd* | nd | nd | 5 |
| Velocity m/sec | 0.51 | 0.54 | 0.53 | 0.58 | 0.55 | 0.53 | 0.60 | 0.58 |
| Reactor Temp. C. | 459 | 460 | 458 | 461 | 458 | 458 | 457 | 457 |
| Reactor Pressure atmospheres | 2.14 | 2.18 | 2.10 | 2.06 | 2.15 | 2.16 | 1.99 | 2.03 |
| Total Solids Loss kg/day | 7.3 | 7.3 | 5.2 | 17.2 | 3.6 | 0.6 | 5.9 | 4.1 |
| % of loss that is inert fines | 0 | 0 | 0 | 0 | nd | nd | nd | 11 |

*not determined

It is seen in both examples that catalyst loses and total solids losses are significantly reduced. Acrylonitrile yields and conversions are not adversely affected.

We claim:

1. In a fluidized bed catalytic reaction process wherein a gaseous feed stream is charged to a fluidized bed of particulate catalyst having a median particle size of 4-80 microns with at least 15% of the catalyst having a particle size less than 44 microns in a reactor system having cyclone means downstream o the fluidized bed for separation of entrained particles from the gaseous stream exiting the fluidized bed, the improvement characterized in that he catalyst is mixed with a discrete inert particulate material present in an amount and having median particle sizes lower than the catalyst median particle size and densities higher than the catalyst density and selected such that particulates exiting the bottom o the last cyclone means in the reactor system comprise at least 5% by weight of said inert particulate material and catalyst losses are at least 25% lower than in an otherwise identical system containing no inert material.

2. The process of claim 1 wherein the catalytic reaction process is a process for ammoxidation of propylene to acrylonitrile in which a gaseous feed stream comprising propylene, ammonia and oxygen is charged to a fluidized bed containing particular ammoxidation catalyst and is reacted to form acrylonitrile.

3. The process of claim 2 wherein eh ammoxidation catalyst is represented by the formula $$Sb_aU_bFe_cBi_dMo_eMe_fO_g$$

wherein Me is nickel or cobalt, a is 1 to 10, b is 0.1 to 5, c is 0.1 to 5, d is 0.001 to 0.1, e is 0.001 to 0.1, f is 0 to 0.1 and g is a number taken to satisfy the quantities and valences of Sb, U, Fe, Bi, Mo and Me present.

4. the process of claim 1 further characterized in that the inert, particulate material has a particle density at least twice that of h catalyst and a mean particle size no greater than the largest particle size of the fourth of the catalyst having the smallest particle sizes.

5. The process of claim 4 wherein the catalytic reaction process is a process for ammoxidation of olefins in which a gaseous feed stream comprising olefins, ammonia and oxygen is charged to a fluidized bed containing particulate ammoxidation catalyst and is reacted to form unsaturated nitriles.

6. The process of claim 5 wherein the catalytic reaction process is a process for ammoxidation of propylene to acrylonitrile in which a gaseous feed stream comprising propylene, ammonia and oxygen is charged to a fluidized bed containing particulate ammoxidation catalyst and is reacted to from acrylonitrile.

7. The process of claim 6 wherein the ammoxidation catalyst is represented by the formula $$Sb_aU_b Fe_cBi_dMo_eMe_fO_g$$

wherein Me is nickel or cobalt, a is 1 to 10, b is 0.1 to 5, c is 0.1 to 5, d is 0.001 to 0.1, e is 0.001 to 0.1, f is 0 to .1 and g is a number taken to satisfy the quantities and valences of Sb, U, Fe, Bi, Mo and Me present.

* * * * *